US012630578B2

(12) United States Patent
Stapley et al.

(10) Patent No.: US 12,630,578 B2
(45) Date of Patent: May 19, 2026

(54) METHODS FOR THE PRODUCTION OF CALCIUM, MAGNESIUM, AND ZINC SALTS OF SUGAR ACIDS

(71) Applicant: DFI USA, LLC, Moses Lake, WA (US)

(72) Inventors: Jonathan Stapley, Mercer Island, WA (US); David Genders, Lancaster, NY (US)

(73) Assignee: DFI USA, LLC, WA (US)

( * ) Notice: Subject to any disclaimer, the term of this patent is extended or adjusted under 35 U.S.C. 154(b) by 1066 days.

(21) Appl. No.: 17/595,875

(22) PCT Filed: May 28, 2020

(86) PCT No.: PCT/US2020/070085
§ 371 (c)(1),
(2) Date: Nov. 29, 2021

(87) PCT Pub. No.: WO2020/243746
PCT Pub. Date: Dec. 3, 2020

(65) Prior Publication Data
US 2022/0235083 A1     Jul. 28, 2022

Related U.S. Application Data

(60) Provisional application No. 62/853,525, filed on May 28, 2019.

(51) Int. Cl.
| | |
|---|---|
| *C07H 1/00* | (2006.01) |
| *B01J 23/52* | (2006.01) |
| *C07H 3/02* | (2006.01) |

(52) U.S. Cl.
CPC .............. *C07H 3/02* (2013.01); *B01J 23/52* (2013.01); *C07H 1/00* (2013.01)

(58) Field of Classification Search
None
See application file for complete search history.

(56) References Cited

U.S. PATENT DOCUMENTS

| | | | |
|---|---|---|---|
| 4,845,208 A | * | 7/1989 | Fuertes ................. C07C 51/235 536/18.5 |
| 5,132,452 A | | 7/1992 | Deller et al. |
| 7,982,031 B2 | | 7/2011 | Kowalczyk et al. |

FOREIGN PATENT DOCUMENTS

| | | | |
|---|---|---|---|
| CN | 102875612 A | * | 1/2013 |
| GB | 1308423 A | | 2/1973 |
| JP | S6021130 B2 | | 5/1985 |
| WO | 2008148549 A2 | | 12/2008 |

OTHER PUBLICATIONS

International Search Report and Written Opinion for corresponding International Application No. PCT/US2020/070085, 6 pages (Aug. 14, 2020).
Notification of Reasons for Refusal for Japanese Patent Application No. 2021-570257, dated May 21, 2024, 5 pages.

* cited by examiner

*Primary Examiner* — Traviss C McIntosh, III
(74) *Attorney, Agent, or Firm* — Ryan L. Marshall; Samantha M. Zeiders-Young; Barnes & Thornburg LLP

(57)     ABSTRACT

A method has now been found for the preparation of calcium, magnesium, and zinc salts of sugar acids, this being the object of the present invention, which is characterized in that the method may include providing a sugar and oxidizing the sugar to a sugar acid in the presence of a noble metal catalyst, oxygen, and a heterogeneous hydroxide source. Preferably the oxidation is carried out with a gold catalyst, and a heterogeneous source of magnesium, calcium, or zinc hydroxide. The oxidation can be performed in a batch or continuous manner.

20 Claims, No Drawings

METHODS FOR THE PRODUCTION OF CALCIUM, MAGNESIUM, AND ZINC SALTS OF SUGAR ACIDS

CROSS-REFERENCED TO RELATED APPLICATIONS

The present application claims the benefit of U.S. Provisional Patent Application No. 62/853,525, filed May 28, 2019, which is hereby incorporated herein by reference in its entirety.

TECHNICAL FIELD

The present disclosure relates to a process of producing high purity calcium, magnesium and zinc salts of sugar acids from sugars, comprising the oxidation of a sugar to a sugar acid in the presence of a catalyst and a heterogenous hydroxide source.

BACKGROUND

Salts of aldonic acids, and the related disaccharides incorporating an aldonic acid, are used industrially for a variety of markets. In particular, gluconic acid salts are widely used. For example, gluconic acid salts are complexing agents and are used in the textile industry, in detergents, and in concrete. They are food additives in beverages and also in bread and feed. Multivalent metal salts of gluconic acid (gluconates) are used for highly bioavailable mineral supplements in food and feed. Gluconic acid salts for food applications and pharmaceutical preparations must be very pure.

Monovalent salts of gluconic acid have been prepared by enzymatic oxidation as in U.S. Pat. Nos. 3,935,071, 4,460, 686, 5,897,995, and 6,828,130. Currently gluconates are produced industrially by fermentation, as in U.S. Pat. Nos. 2,602,768, and 6,416,981. Calcium, magnesium, and zinc salts of sugar acids have been produced by ion-exchanging monovalent salts with multivalent metal salts as in U.S. Pat. No. 3,670,000 or by neutralizing gluconic acid or its lactone with multivalent metal hydroxides. Biotechnological approaches to producing sugar acid salts are complicated by the specificity of the enzymes or fermentation conditions for particular molecules and salt concentrations. Consequently the production of multivalent salts of sugar acids from biotechnological routes are often less efficient as in U.S. Pat. No. 7,618,664, in Lu, et al., Enzyme and Microbial Technology (1996): 339-342, in Bao, et al., Chemical Engineering Science, 6165-6170 (2001), and in Chinese Patent No. 1,054,161.

As biotechnological approaches to sugar acid production are extremely specific for the starting sugars, the enzymatic or fermentation conditions that readily produce sodium gluconate from glucose are entirely ineffective in the oxidation of other sugars to sugar acids. Alternatively, noble metal catalysts have been widely described in the literature as oxidizing aldoses to sodium salts of aldonic acids. Gold catalysts in particular have shown to be very effective for the oxidation of glucose to sodium gluconate as described by Theilecke, et al, Catalysis Today, 115-120 (2007). Galactose has been oxidized to the sodium galactonate as described by Kusema, et al., ChemCatChem, 1789-1798 (2011). In these applications a sugar solution is provided and mixed with the heterogenous catalyst under pressurized oxygen. A specific alkaline pH in the reaction is maintained during the reaction by the addition of a sodium hydroxide solution and the reactions occur in a fraction of the time needed for biotechnological oxidations. Moreover the resulting product solution is free from the contaminants associated with fermentations, which results in less purification needed for a pure final product. Calcium, magnesium, and zinc hydroxides are only sparingly soluble, with saturated solutions having a concentration of only a small fraction of 1%. A need in the art exists, therefore, for a flexible method to efficiently produce calcium, magnesium, and zinc salts of sugar acids at high concentrations and purity.

SUMMARY

A method has now been found for the preparation of calcium, magnesium, and zinc salts of sugar acids, this being the object of the present invention, which is characterized in that it comprises the following stages: a sugar is provided, preferably in a concentration greater than 0.5 M; the sugar is oxidized to a sugar acid in the presence of a noble metal catalyst, oxygen, and a heterogeneous hydroxide source. Preferably the oxidation is carried out with a gold catalyst, and a heterogeneous source of magnesium, calcium, or zinc hydroxide. The oxidation can be performed in a batch or continuous manner.

DETAILED DESCRIPTION

Various embodiments are described below. The relationship and functioning of the various elements of the embodiments may better be understood by reference to the following detailed description. Embodiments, however, are not limited to those illustrated below. In certain instances details may have been omitted that are not necessary for an understanding of embodiments disclosed herein.

Definitions

As used herein, the term sugar refers to an aldose or a disaccharide that include an aldose with a free aldehyde. Examples of sugars include glucose, galactose, xylose, arabinose, L-threose, lactose, and maltose.

As used herein, the term sugar acid refers to an aldonic acid or a disaccharide that includes and aldonic acid, and salts thereof. Examples of sugar acids include gluconic acid, galactonic acid, xylonic acid, arabinonic acid, lactobionic acid, and maltiobionic acid.

As used herein, heterogeneous hydroxide source refers to a heterogenous source of magnesium hydroxide, calcium hydroxide, or zinc hydroxide.

As used herein, heterogeneous source of magnesium hydroxide refers to magnesium hydroxide, magnesium oxide, or magnesium carbonate.

As used herein, heterogeneous source of calcium hydroxide refers to calcium oxide, calcium hydroxide, or calcium carbonate.

As used herein, heterogeneous source of zinc hydroxide refers to zinc hydroxide carbonate (a compound with a formula of $[ZnCO_3]_2 \cdot [Zn(OH)_2]_3$), zinc hydroxide, or zinc oxide.

The term "oxidation" as used herein refers to the conversion of an aldehyde group (—CHO) of a sugar to a carboxyl group (—COOH) by a chemical reaction or physical process.

The term oxygen as used herein refers to molecular oxygen ($O_2$). Oxygen may be provided as a gas alone or as constituent of mixture of gases such as exist in atmospheric air.

Providing a Sugar

The sugar is a raw material for the production of a sugar acid salt. Sugars are readily available compounds and can be produced from many raw materials. For example, glucose is commonly available from the hydrolysis of starch; lactose can be produced from milk; glucose and galactose can be produced from lactose or biomass hydrolysis; and xylose can be produced from biomass hydrolysis. Hydrolyses of raw materials that produce sugars can be performed commercially either enzymatically or chemically. Other synthetic routes to sugar production are also common.

In some embodiments, the sugar may be glucose, galactose, xylose, arabinose, lactose, or maltose. In some embodiments, the sugar may be glucose. In some embodiments, the sugar may be galactose. In some embodiments, the sugar may be xylose. In some embodiments, the sugar may be arabinose. In some embodiments, the sugar may be lactose. In some embodiments, the sugar may be maltose.

Preferably the sugar is provided in a solution with a concentration greater than 0.1 M, and more preferably with a concentration greater than 0.5 M. In some aspects, the concentration of the sugar may be from about 0.1 M to about 7 M. In some aspects, the concentration of the sugar may be from about 0.5 M to about 5 M, about 0.5 M to about 4 M, about 0.5 M to about 3 M, about 0.5 M to about 2 M, or about 0.1 M to about 1 M. In some aspects, the solution may be an aqueous solution.

Sugar Oxidation

The method of producing a salt of a sugar acid may include oxidizing a sugar to a sugar acid in the presence of a noble metal catalyst, oxygen, and a heterogeneous source of hydroxide. In some aspects, the heterogeneous source of hydroxide may be a heterogeneous source of magnesium hydroxide, calcium hydroxide, or zinc hydroxide. Preferably the noble metal catalyst is a gold catalyst. The sugar acid product is formed as the metal salt associated with the hydroxide used in the reaction.

In some embodiments, sugar acid oxidation may be performed in a batch reaction where all the heterogenous hydroxide source required for the reaction is added at the beginning of the reaction.

In other embodiments, sugar oxidation may be performed in a batch reaction where a slurry of the heterogenous hydroxide source and water are metered into the reaction over time.

In another embodiment, sugar oxidation may be performed in a continuous reaction where a slurry of the heterogenous hydroxide source and either water or sugar solution are added during the reaction. In another embodiment, sugar oxidation may be performed in a continuous reaction where an excess of heterogenous hydroxide source is maintained in the reaction chamber resulting in a heterogenous hydroxide cation to sugar ratio greater than 1:2. In some aspects, the heterogenous hydroxide cation to sugar ratio may be from about 1:2 to about 1000:1. In some aspects, the heterogenous hydroxide to sugar ratio may be about 1:2, about 5:1, about 50:1, or about 500:1.

In some aspects, the reaction vessel may be pressurized with oxygen to a pressure of about 60 psi to about 200 psi. In some aspects, the reaction vessel may be may be pressurized with oxygen to a pressure of about 70 psi, about 80 psi, about 90 psi, about 100 psi, about 110 psi, about 120 psi, about 130 psi, about 140 psi, or about 150 psi.

In some aspects, the temperature of the reaction solution may be about 30° C. to about 70° C. In some aspects, the temperature of the reaction solution may be about 40° C., about 50° C., or about 60° C.

In some aspects, the resulting concentration of the salt of the sugar acid in the reaction solution may be from about 0.1 M to about 1 M. In some aspects, the resulting concentration of the salt of the sugar acid in the reaction solution may be from about 0.2 M, about 0.3 M, about 0.4 M, or about 0.5 M.

In some aspects, the oxidation may be carried out as a batch reaction. In the batch reaction, all of the heterogeneous hydroxide source may be added at a beginning of the batch reaction. In some aspects, the heterogeneous hydroxide source may be added during the batch reaction.

In some aspects, the oxidation may be carried out as a continuous reaction. For a continuous reaction, the heterogeneous hydroxide source may be added during the continuous reaction. In some aspects, the reactor may be charged with an excess amount of the heterogeneous hydroxide source and the sugar may be fed into the reactor continuously.

EXAMPLES

Example 1

A 0.60 M solution of glucose was provided. A 1 liter pressure vessel was provided to which the glucose solution was added and dosed with 4 g per liter of a 4.5 wt % of gold in the catalyst, and 17.5 g per liter magnesium hydroxide. The reaction vessel was pressurized with oxygen at 100 psi, and the temperature was raised to 50° C. The reaction was stirred for 2.9 hrs, after which it was cooled to room temperature and analyzed. The resulting solution had a 0.30 M concentration of magnesium gluconate, which constituted a 100% yield.

Example 2

A 0.68 M solution of glucose was provided. A 1.5 liter pressure vessel was proved capable of running in continuous mode. The reactor was charged with 900 ml of glucose solution along with 8 g per liter of a 4.5% gold catalyst and 19.8 g per liter of magnesium hydroxide. The reaction vessel was pressurized with 100 psi oxygen, and the temperature was raised to 70° C. After 1.5 hrs, the reaction began to operate in continuous mode by the addition of a glucose solution (0.70 M):magnesium hydroxide slurry (19.7 g per liter) at a rate of 5 ml per minute. Product solution was removed from the reaction vessel at a rate of approximately 5 ml per minute. The reaction proceeded for another 5.5 hrs. The resulting product solution had a concentration of 0.30 M magnesium gluconate, which constituted an 88% yield.

Example 3

A 0.5 M solution glucose was provided. In five separate experiments, a 1 liter pressure vessel was provided to which 0.5 liters of glucose solution was added and dosed with 4 g per liter of a 4.5% gold catalyst, and a heterogeneous hydroxide source as listed in Table 1. The reaction vessel was pressurized with oxygen at 100 psi. The reaction temperature and times of each experiment are given in Table 1, along with the respective glucose conversion and selectivity of each experiment.

TABLE 1

| Product | Heterogeneous Hydroxide Source | Heterogeneous Hydroxide (g) | Temperature (C.) | Reaction Tiem (hr) | Glucose Conversion (%) | Glucose Selectivity (%) |
|---|---|---|---|---|---|---|
| Zinc Gluconate | Zinc Oxide | 18.1 | 60 | 3.6 | 35 | 94 |
| Zinc Gluconate | Zinc Hydroxide Carbonate | 124.9 | 60 | 5.3 | 26 | 85 |
| Calcium Gluconate | Calcium Carbonate | 22.5 | 90 | 5.6 | 89 | 90 |
| Calcium Gluconate | Calcium Hydroxide | 9.3 | 50 | 3.5 | 97 | 95 |
| Magnesium Gluconate | Magnesium Hydroxide | 6.9 | 70 | 4.0 | 96 | 100 |
| Magnesium Xylonate | Magnesium Hydroxide | 6.9 | 50 | 3.7 | 90 | 82 |
| Magnesiom Lactobionate | Magnesium Hydroxide | 6.9 | 50 | 6.0 | 89 | 87 |
| Magnesium L-Threonate | Magnesium Hydroxide | 6.9 | 70 | 3.00 | 100 | 99 |

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a sugar" is intended to include "at least one sugar" or "one or more sugars."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

STATEMENTS

1. A method of producing a salt of a sugar acid, comprising:
oxidizing a sugar to produce a sugar acid in the presence of a noble metal catalyst, oxygen, and a heterogeneous hydroxide source in a reaction vessel.
2. The method of 1 wherein the noble metal catalyst is a gold catalyst.
3. The method of any one of 1-2, wherein the oxidation is carried out as a batch reaction, and in which all the heterogeneous hydroxide source is added at a beginning of the batch reaction.
4. The method of any one of 1-2, wherein the oxidation is carried out as a batch reaction, and in which the heterogeneous hydroxide source is added during the batch reaction.
5. The method of any one of 1-2, wherein the oxidation is carried out as a continuous reaction, and in which the heterogeneous hydroxide source is added during the continuous reaction.
6. The method of any one of 1-2, wherein the oxidation is carried out as a continuous reaction, and in which the heterogeneous hydroxide source is present in a molar ratio greater than 1:2 with the sugar.

7. The method of any one of 1-6, wherein the heterogeneous hydroxide source is magnesium hydroxide, calcium hydroxide, or zinc hydroxide carbonate.
8. The method of any one of 1-7, wherein the heterogeneous hydroxide source is magnesium hydroxide, magnesium oxide, or magnesium carbonate.
9. The method of any one of 1-7, wherein the heterogeneous hydroxide source is calcium oxide, calcium hydroxide, or calcium carbonate.
10. The method of any one of 1-7, wherein the heterogeneous hydroxide source is zinc hydroxide carbonate, zinc hydroxide, or zinc oxide.
11. The method of any one of 1-10, wherein the sugar acid is an aldonic acid or a disaccharide that comprises an aldonic acid.
12. The method of any one of 1-11, wherein the sugar acid is gluconic acid, galactonic acid, xylonic acid, arabinonic acid, L-threonic acid, lactobionic acid, or maltiobionic acid.
13. The method of any one of 1-12, wherein the reaction vessel may be pressurized with oxygen to a pressure of about 60 psi to about 200 psi.
14. The method of any one of 1-13, wherein a temperature of the reaction solution may be about 30° C. to about 70° C.
15. The method of any one of 1-14, wherein the salt of the sugar acid is zinc gluconate, calcium gluconate, magnesium gluconate, magnesium xylonate, magnesium L-threonate, or magnesium lactobionate.
16. The method of any one of 1-15, wherein the sugar is glucose, galactose, xylose, arabinose, L-threose, lactose, or maltose.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:
1. A method of producing a salt of a sugar acid, comprising:
oxidizing a sugar to produce a sugar acid in the presence of a noble metal catalyst, oxygen, and a heterogeneous hydroxide source in a reaction vessel,
wherein the heterogeneous hydroxide source is magnesium hydroxide, magnesium oxide, magnesium carbonate, calcium hydroxide, calcium oxide, calcium carbonate, zinc hydroxide, zinc oxide, or zinc carbonate.

2. The method of claim 1 wherein the noble metal catalyst is a gold catalyst.

3. The method of claim 1, wherein the oxidation is carried out as a batch reaction, and in which all the heterogeneous hydroxide source is added at a beginning of the batch reaction.

4. The method of claim 1, wherein the oxidation is carried out as a batch reaction, and in which the heterogeneous hydroxide source is added during the batch reaction.

5. The method of claim 1, wherein the oxidation is carried out as a continuous reaction, and in which the heterogeneous hydroxide source is added during the continuous reaction.

6. The method of claim 1, wherein the oxidation is carried out as a continuous reaction, and in which the heterogeneous hydroxide source is present in a molar ratio greater than 1:2 with the sugar.

7. The method of claim 1, wherein the heterogeneous hydroxide source is magnesium hydroxide, magnesium oxide, or magnesium carbonate.

8. The method of claim 1, wherein the heterogeneous hydroxide source is calcium oxide, calcium hydroxide, or calcium carbonate.

9. The method of claim 1, wherein the heterogeneous hydroxide source is zinc hydroxide carbonate, zinc hydroxide, or zinc oxide.

10. The method of claim 1, wherein the sugar acid is an aldonic acid or a disaccharide that comprises an aldonic acid.

11. The method of claim 1, wherein the sugar acid is gluconic acid, galactonic acid, xylonic acid, arabinonic acid, L-threonic acid, lactobionic acid, or maltiobionic acid.

12. The method of claim 1, wherein the reaction vessel may be pressurized with oxygen to a pressure of about 60 psi to about 200 psi.

13. The method of claim 1, wherein a temperature of the reaction solution may be about 30° C. to about 70° C.

14. The method of claim 1, wherein the salt of the sugar acid is zinc gluconate, calcium gluconate, magnesium gluconate, magnesium xylonate, magnesium L-threonate, or magnesium lactobionate.

15. The method of claim 1, wherein the sugar is glucose, galactose, xylose, arabinose, L-threose, lactose, or maltose.

16. A method of producing a salt of a sugar acid, comprising:

oxidizing a sugar to produce a sugar acid in the presence of a noble metal catalyst, oxygen, and a heterogeneous hydroxide source in a reaction vessel, wherein the heterogeneous hydroxide source is magnesium hydroxide, magnesium oxide, magnesium carbonate, calcium hydroxide, calcium oxide, calcium carbonate, zinc hydroxide, zinc oxide, or zinc carbonate;

wherein the oxidation is carried out as a continuous reaction, and in which the heterogeneous hydroxide source is added during the continuous reaction; and wherein the heterogeneous hydroxide source is present in a molar ratio greater than 1:2 with the sugar; and wherein the reaction vessel may be pressurized with oxygen to a pressure of about 60 psi to about 200 psi.

17. The method of claim 16, wherein the noble metal catalyst is a gold catalyst.

18. The method of claim 16, wherein a temperature of the reaction solution may be about 30° C. to about 70° C.

19. The method of claim 16, wherein the sugar acid is an aldonic acid or a disaccharide that comprises an aldonic acid.

20. The method of claim 16, wherein the sugar acid is gluconic acid, galactonic acid, xylonic acid, arabinonic acid, L-threonic acid, lactobionic acid, or maltiobionic acid.

* * * * *